United States Patent [19]

McCarthy

[11] Patent Number: 5,549,706
[45] Date of Patent: Aug. 27, 1996

[54] MODULAR HIP PROSTHESIS

[75] Inventor: Thomas F. McCarthy, Neshanic Station, N.J.

[73] Assignee: Howmedica Inc., New York, N.Y.

[21] Appl. No.: 420,394

[22] Filed: Apr. 10, 1995

Related U.S. Application Data

[63] Continuation of Ser. No. 15,119, Feb. 9, 1993, abandoned.

[51] Int. Cl.⁶ ..................................................... A61F 2/36
[52] U.S. Cl. ............................................... 623/23; 623/18
[58] Field of Search ................................ 623/16, 18, 19, 623/20, 22, 23, 66

[56] References Cited

U.S. PATENT DOCUMENTS

| | | | |
|---|---|---|---|
| 4,608,055 | 8/1986 | Morrey et al. | 623/23 |
| 4,728,333 | 3/1988 | Masse et al. | 623/23 |
| 4,770,660 | 9/1988 | Averill | 623/23 |
| 4,842,606 | 6/1989 | Kranz et al. | 623/23 |
| 4,938,772 | 7/1990 | Frey et al. | 623/23 |
| 5,092,900 | 3/1992 | Marchette et al. | 623/23 |
| 5,201,769 | 4/1993 | Schutzer | 623/23 |

FOREIGN PATENT DOCUMENTS

| | | |
|---|---|---|
| 0201442 | 11/1986 | European Pat. Off. . |
| 0257359 | 2/1988 | European Pat. Off. . |
| 0273871 | 6/1988 | European Pat. Off. . |
| 0366945 | 5/1990 | European Pat. Off. . |
| 0404716 | 12/1990 | European Pat. Off. .................. 623/23 |
| 0447734 | 9/1991 | European Pat. Off. . |
| 2633509 | 1/1990 | France . |
| 2644690 | 9/1990 | France . |
| 2668058 | 4/1992 | France . |
| 4126837 | 11/1992 | Germany . |
| 8603962 | 7/1986 | WIPO ..................................... 623/23 |
| WO88/01854 | 3/1988 | WIPO . |
| 9117723 | 11/1991 | WIPO ..................................... 623/23 |
| WO92/03993 | 3/1992 | WIPO . |
| WO92/19186 | 11/1992 | WIPO . |

OTHER PUBLICATIONS

Product Brochure, Design Advantages, Richards Modular Hip System, undated.

Primary Examiner—David Isabella
Attorney, Agent, or Firm—Pennie & Edmonds

[57] ABSTRACT

A femoral hip prosthesis comprises a main member, a modular member and a means for connecting the two. The main member has a stem portion and a body portion which are adapted for insertion into the intramedullary canal. The body portion has lateral, posterior, and anterior sides adapted to mate with the bone and has a medial side configured and dimensioned to receive a modular member. The modular member is chosen from a plurality of such members of various shapes and sizes and is adapted to fit accurately into the intramedullary canal, especially after the intramedullary canal has been deformed through the prior implantation of a prosthetic hip device.

20 Claims, 4 Drawing Sheets

MODULAR HIP PROSTHESIS

This is a file wrapper continuation of application Ser. No. 08/015,119, filed Feb. 9, 1993, now abandoned.

BACKGROUND OF THE INVENTION

The present invention relates to a hip prosthesis and more particularly to a modular femoral component for a hip prosthesis designed to adapt for an accurate fit in the intramedullary canal, particularly in revision surgery.

The prior art contains many hip prostheses which are constructed to replace the upper portion of the femur. The conventional prosthesis is an unitary structure which is designed to be inserted into the intramedullary canal. To function properly, the prosthetic device must fit snugly into the intramedullary canal. If the fit is loose then the prosthesis will shift positions in relation to the femur causing pain to the patient, interfering with the transmission of power to the leg, and making the hip more vulnerable to re-injury. Because of these problems much of the art attempts to improve the fit of the prosthetic device in the intramedullary canal.

The use of a prosthesis which is constructed of discrete parts is known in the art. Such a prosthesis is shown in European Patent Application No. 257,359 which discloses a discrete stem, body, neck and capitulum. This design is intended to allow the doctor to assemble a prosthesis at the time of implantation.

The use of various inserts in an attempt to obtain a more accurate fit in the intramedullary canal is known in the art. One prosthesis with an insert design is shown in European Patent Application No. 273,871 which discloses a U-shaped insert that wraps around the prosthesis. This design is intended to allow a prosthesis to be used with either the left or right femur depending on the geometry of the U-shaped insert.

Another prosthesis with an insert design is shown in French Patent No. 2,633,509 which discloses the use of inserts on the anterior and posterior surfaces of the prosthesis. The disclosed inserts are intended to more snugly contact the anterior and posterior surfaces of the intramedullary canal.

One problem in the use of prosthetic hip devices is that, following the implantation of the prosthetic device, the intramedullary canal can flair or deform due to osteolysis. The flared or deformed intramedullary canal no longer accurately mates with the prosthetic device and revision surgery is required to replace the originally implanted prosthesis with a more snugly fitting substitute. The solutions proposed in the references discussed above do not adequately address this problem.

There exists, therefore, a need in the art for an improved hip prosthesis which permits a surgeon to modify, during revision surgery, the geometry of the medial portion of the prosthetic device to create a more accurate fit with the deformed or flared intramedullary canal.

SUMMARY OF THE INVENTION

It is therefore an object of the present invention to provide means through which the geometry of the medial portion of a hip prosthesis can be easily altered to more accurately fit into an intramedullary canal which has been deformed or flared. This object is accomplished by having a modular member located in the medial portion of the prosthetic device which can be replaced by choosing an appropriately sized and adapted modular member. Such modularity allows the revision surgery physician to easily customize the prosthesis to regain an accurate fit in the deformed or flared intramedullary canal. A further advantage of the current invention is that it eliminates the burdensome inventory requirements necessitated by using integral prosthetic devices. This is because the prosthetic members are adapted to receive more than one modular medial member.

In accordance with the present invention, a femoral hip prosthesis comprises a first or main member which possesses a stem portion and a body portion adapted for insertion into the intramedullary canal. The body portion has lateral, posterior, and anterior sides which are adapted to mate with the bone and has a medial side configured and dimensioned for receiving another member. Additionally, the invention comprises a second or modular member. The modular member may be chosen from a plurality of such members having anterior, posterior, and medial sides which are adapted for an accurate fit in the intramedullary canal, and a lateral side configured and dimensioned complimentarily to the medial side of the body portion. The invention also comprises a means for connecting the medial side of the body portion with the lateral side of the modular member.

Also in accordance with the present invention, a kit for the assembly of a hip prosthesis comprises a plurality of first or main members each with a stem portion and a body portion adapted for insertion in the intramedullary canal. The body portions have lateral, posterior, and anterior sides which are adapted to mate with the bone and a medial side configured and dimensioned for receiving another member. Additionally, the invention comprises a plurality of second or modular members. The modular members have anterior, posterior, and medial sides which are adapted for an accurate fit in the intramedullary canal and a lateral side that is configured and dimensioned complimentarily to the medial side of the body portion. The invention also comprises means for connecting the medial side of the body portions with the lateral side of the modular members.

DETAILED DESCRIPTION OF THE INVENTION

Figure 1:
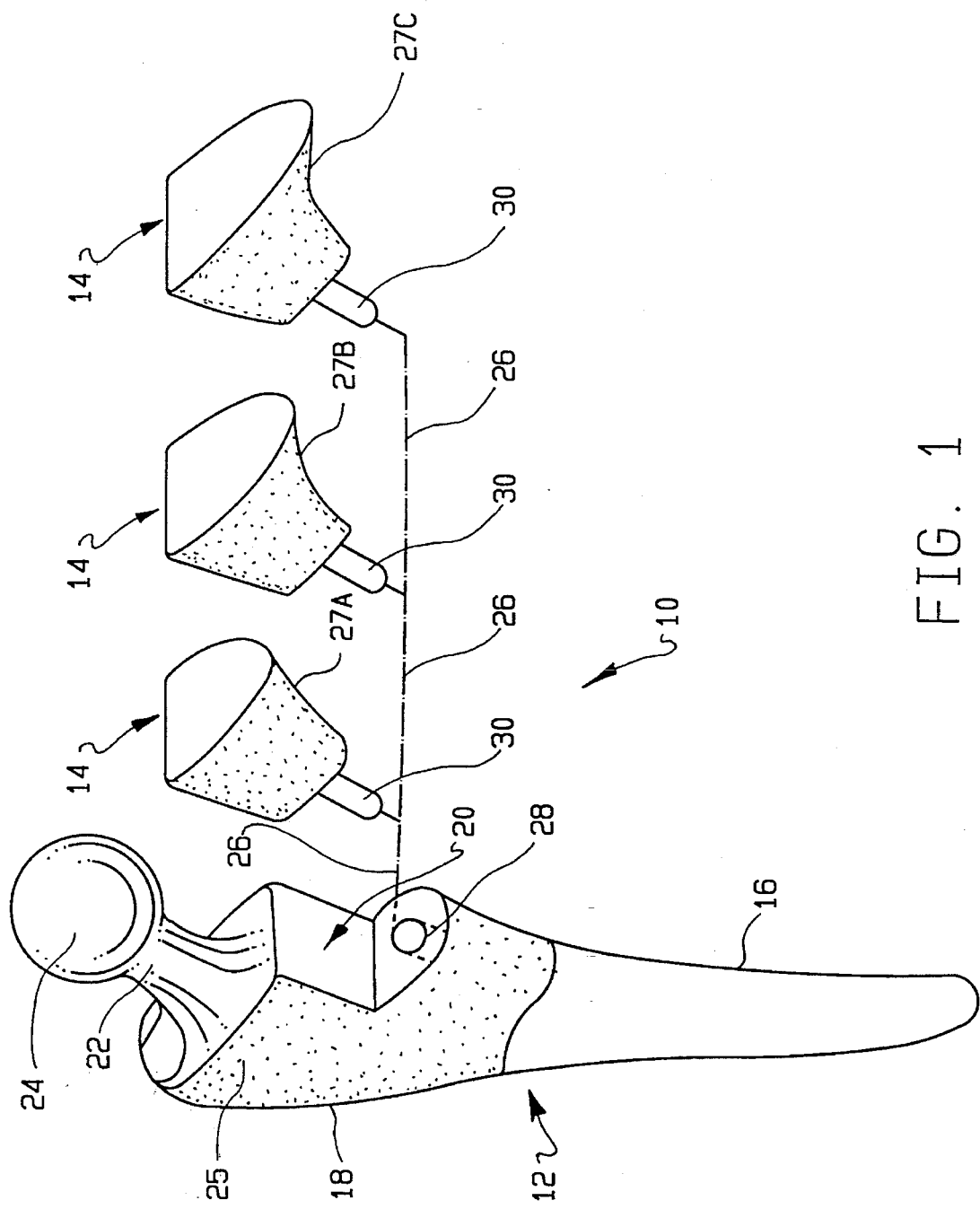
FIG. 1 is an exploded perspective view of one embodiment of a femoral hip prosthesis according to the present invention, illustrating different modular members.

Referring to FIG. 1, femoral hip prosthesis 10 generally includes main member 12 and modular member 14. Prosthesis 10 is shown in FIG. 1 with a selection of differently shaped modular members 14, such as may be provided with a kit according to the present invention. Main member 12 includes stem portion 16, body portion 18, neck portion 22 and capitulum 24. On the proximal medial face of body portion 18, recessed area 20 is shaped to receive modular member 14. The remaining surfaces of body portion 18 are conventional and may include porous coating 25 or other surface treatment, such as hydroxylapatite, to encourage bone ingrowth.

Modular member 14 also has anterior, posterior and medial faces which may be covered with an appropriate bone ingrowth surface or material. However, the lateral and lower faces of the modular member are configured and dimensioned to securely mate with recessed area 20 on main member 12. In order to provide the necessary improved fit in the intramedullary canal, different sizes and shapes of modular members are provided, each of which is configured and dimensioned to securely mate with the same main member. For example, FIG. 1 shows three alternative modular members with progressively increasing flared medial faces 27A, B and C, respectively. A kit containing a variety of such flared modular members is well suited for addressing the problems frequently encountered with flared intramedullary canals in revision surgery.

In order to secure together main member 12 and modular member 14, connection means 26 are provided. As shown in FIG. 1, connection means 26 comprises hole 28 in main member 12, which receives extending element 30 mounted on modular member 14. Preferably, one or both of hole 28 and element 30 are tapered to create a secure interference fit. Such interference fits are well known in the art and can be easily specified by a person of ordinary skill.

Figure 2:
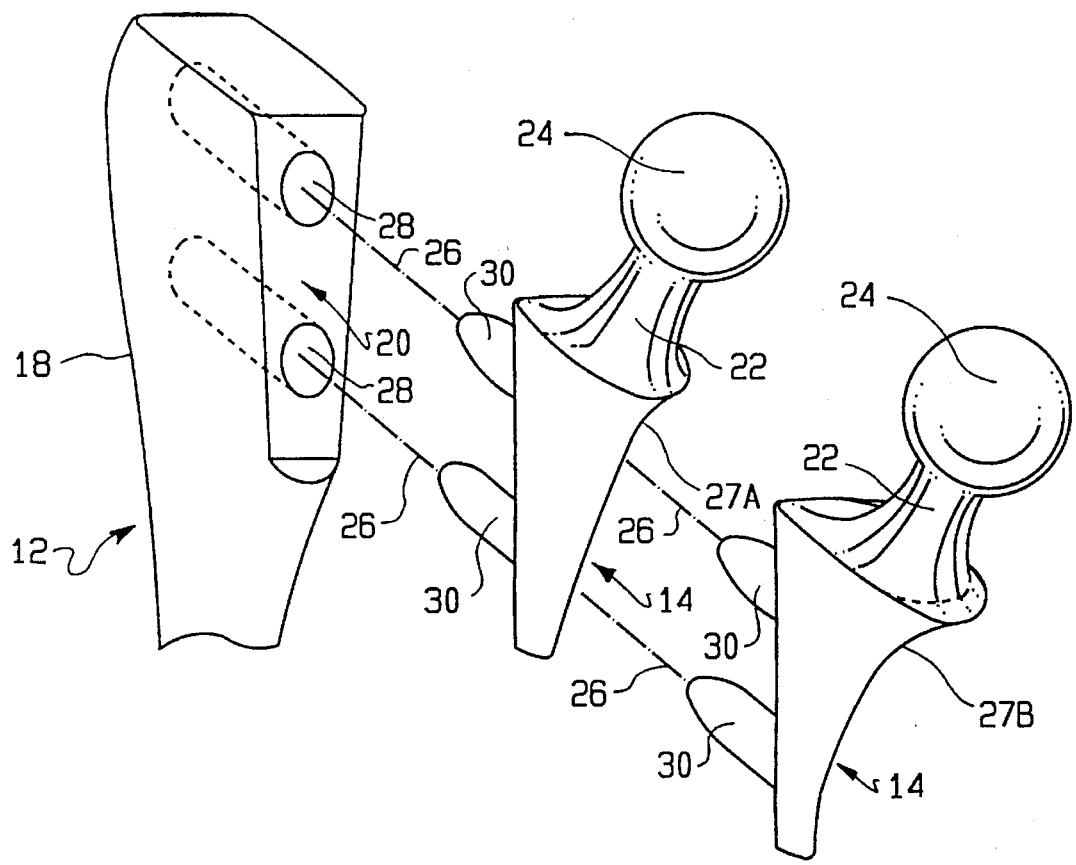
FIG. 2 is an exploded perspective view of an alternative embodiment of a femoral hip prosthesis according to the present invention, also illustrating different modular members.

One alternative embodiment of the present invention is shown in FIG. 2. Body portion 18 is again provided recessed area 20 for receiving modular member 14 on the medial face. However, in this embodiment, modular member 14 includes capitulum 24 and neck portion 22. Instead of being disposed on the lower face of the modular member, elements 30 (of which there are two in the illustrated embodiment) are disposed on the lateral face and are received in corresponding holes 28 of connection means 26 on the medial face of member 12. Again, an interference fit may be provided. Otherwise, the embodiment of FIG. 2 is substantially the same as the embodiment of FIG. 1. Although not specifically illustrated, bone ingrowth surfaces can be provided as described above.

Figure 3:
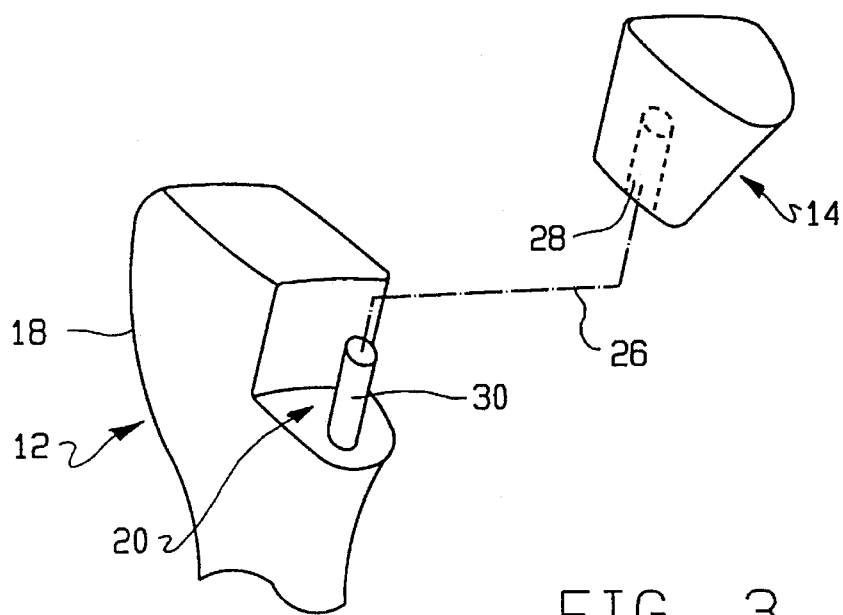
FIGS. 3–10 are exploded perspective views of the body portion and modular member of different alternative embodiments of femoral hip prostheses according to the present invention, illustrating alternative means for connecting the main and modular members.
Figure 4:
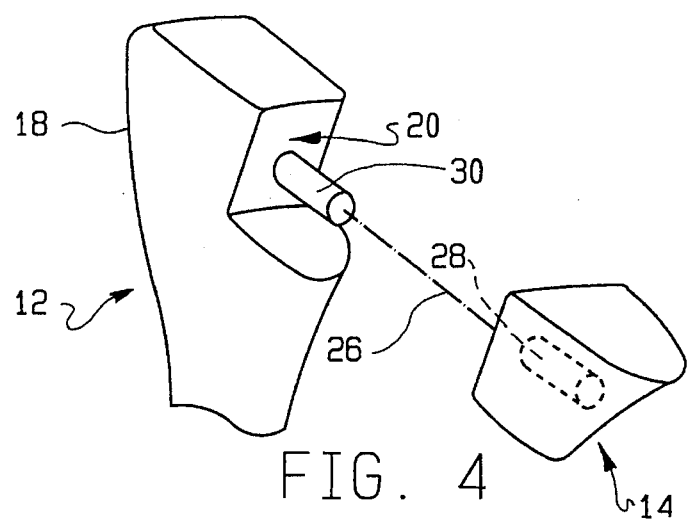

FIGS. 3–10 illustrate further alternative preferred embodiments of the present invention and in particular different connection means 26. Not shown in FIGS. 3–10 are bone ingrowth surfaces or the capitulum and neck portion. However, these may be provided in each of the embodiments discussed below according to the teachings of either of FIGS. 1 or 2. Referring first to FIG. 3, connection means 26 is similar to that shown in FIG. 1 except that hole 28 is disposed in modular member 14 and element 30 extends from main member 12. The embodiment shown in FIG. 4 is also similar to that of FIG. 2, except that connection means 26 includes only a single hole 28 and element 30. Also the hole and element are disposed on opposite members from that disclosed in FIG. 2.

Figure 5:
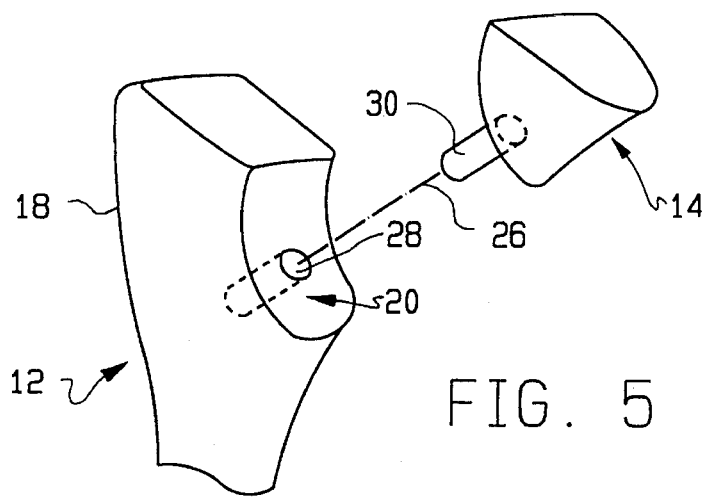

Connection means 26 as shown in FIG. 5 is substantially the same as illustrated in FIG. 1. However, as shown in FIG. 5, recessed area 20 is gradually curved, as opposed to having flat, planar surfaces. In general, recessed area 20 may be any shape which allows main member 12 and modular member 14 to fit securely and snugly together with substantially no open space therebetween, and which is also configured to prevent rotation between the two members.

Figure 6:
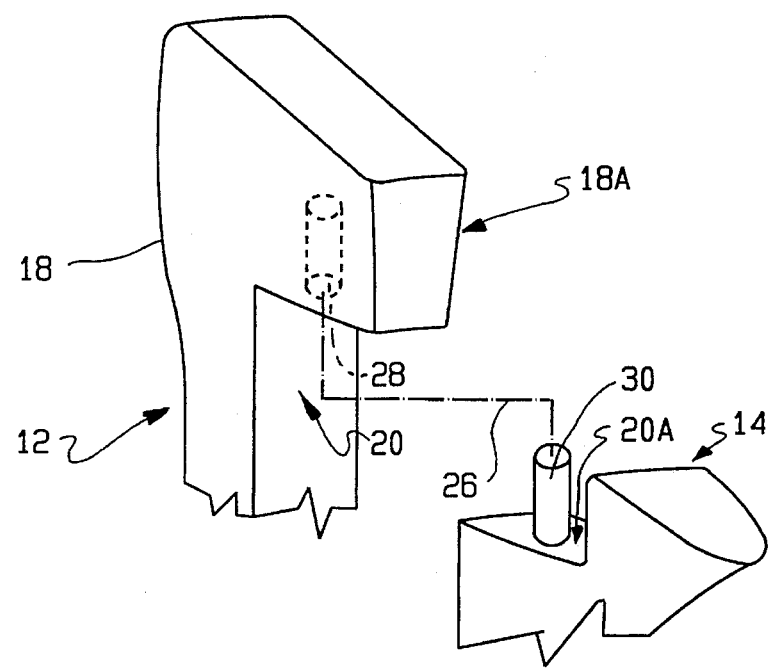

Referring to FIG. 6, body portion 18 has an outwardly extending medial portion 18A which provides a lower surface on which hole 28 is disposed. Recessed area 20 is thus inverted as compared to FIGS. 1 and 2. Modular member 14 has a complimentary recessed area 20A which mates with recess 20 and extending medial portion 18A. This embodiment allows modular member 14 to cover substantially the entire medial face of the body portion of the prosthesis.

Figure 7:
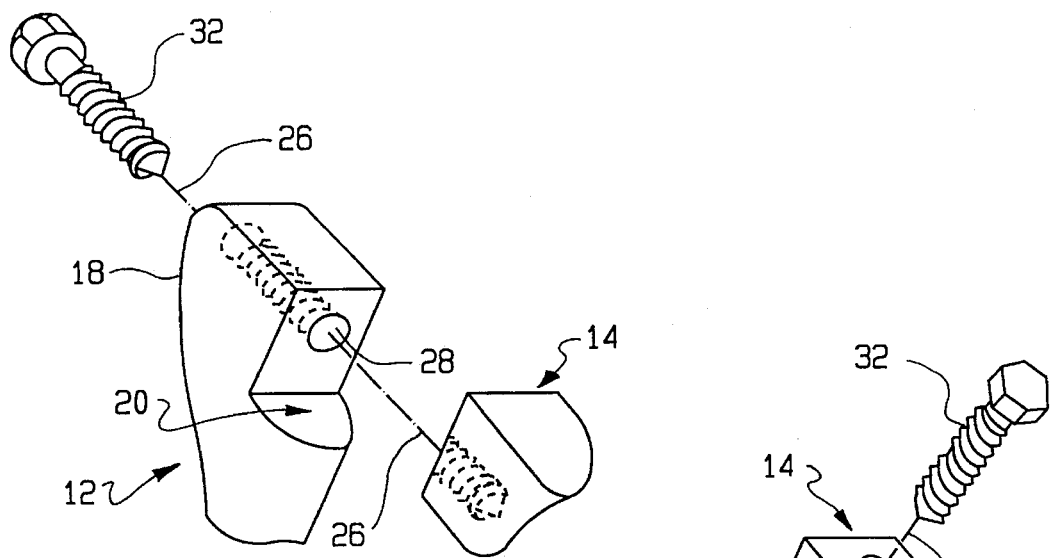
Figure 8:
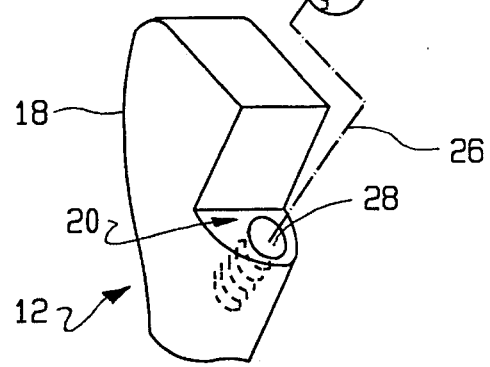

Referring to FIG. 7, body portion 18 has connection means 26 including threaded fastener 32 which passes through hole 28 in body portion 18 and is received in a threaded hole in modular member 14. Such a connection means, employing threaded fasteners, eliminates the need for interference fits which may be difficult to disassemble during surgery if an incorrectly sized modular member is initially selected. Threaded fasteners also provide a positive mechanical connection and can be used in conjunction with appropriate interference fits. In the embodiment of FIG. 8, connection means 26 comprises threaded fastener 32 which passes through modular member 14 and is received in threaded hole 28 in main member 12. The main and modular members and recess 20 are configured such that hole 28 opens on a plane other than that of the medial face or parallel thereto.

Figure 9:
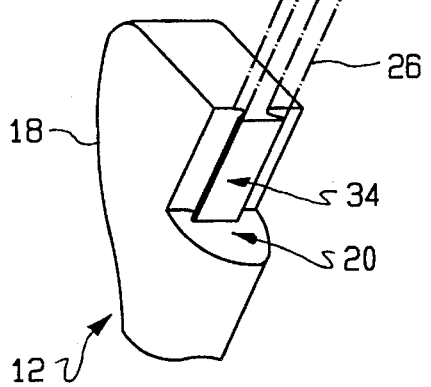
Figure 10:
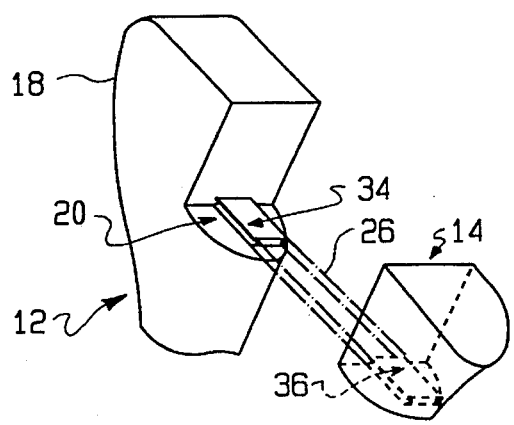

FIGS. 9 and 10 show further alternative embodiments wherein connection means 26 comprises dovetail 34 and complimentary groove 36. As with hole 28 and element 30, the dovetail and groove can be located on different faces of the modular and main members. The dovetail and groove also may be dimensioned to provide an interference fit.

The kit of the present invention includes one or more main members 12 and a plurality of modular members 14 adapted to connect therewith. Any of the connection means described above may be utilized. Also, a person of ordinary skill in the art could provide further connection means in accordance with the teachings of the present invention. Typically, a kit for use in revision surgery will include a variety of modular members having incrementally increasing flared medial faces such as shown in FIG. 1. Such flared modular members are preferably designed with a medial face that makes a smooth transition into the medial face of the main member, either the body portion or the shaft. The kit may also include a holder and sterile packaging for contents of the kit and tools, accessories or equipment necessary or convenient for the implementation of the present invention.

I claim:

1. A femoral hip prosthesis comprising:
   a first member having,
      a stem portion adapted for insertion into the intramedullary canal, and
      a body portion proximal to the stem portion and adapted for insertion into the intramedullary canal, the body portion forming lateral, posterior and anterior outer side surfaces of the prosthesis and configured and dimensioned for an accurate fit in the intramedullary canal, said body portion further having a medial side;
   a second member forming anterior, posterior and medial outer side surfaces of the prothesis and configured and dimensioned for an accurate fit in the intramedullary canal, said second member further having a lateral side; and
   means for connecting the lateral side of the second member with the medial side of the body portion of the first member such that the combination of the body portion of the first member with the second member forms the anterior and posterior outer side surfaces of the body of the prothesis, the combination configured and dimensioned to accurately fit the intramedullary canal.

2. The prosthesis as in claim 1, wherein the first member includes:

a proximally extending neck portion; and a capitulum on the neck portion.

3. The prosthesis as in claim 1, wherein the second member includes:

a proximally extending neck portion; and a capitulum on the neck portion.

4. The prosthesis as in claim 1, wherein:

the medial side of the body portion defines a recess configured and dimensioned to receive the lateral side of the second member, said lateral side of the second member having a shape complimentary therewith; and said connection means includes an element extending from one said members and received in a complimentarily shaped void defined by the other said members.

5. The prosthesis as in claim 4, wherein said element comprises a member sized for an interference fit in said void.

6. The prosthesis as in claim 5, wherein said member comprises a dovetail.

7. The prosthesis as in claim 4, wherein said element comprises a threaded fastener passing through one said member and said void comprises a threaded hole.

8. The prosthesis as in claim 4, wherein said recess is defined by a first substantially planar surface on the medial face and a second substantially planar surface disposed at an angle thereto and approximately perpendicular to the anterior and posterior sides.

9. The prosthesis as in claim 8, wherein said recess opens proximally and medially with respect to the first member.

10. The prosthesis as in claim 8, wherein said recess opens distally and medially with respect to the first member.

11. A kit for the assembly of a femoral hip prothesis, the kit comprising:

at least one first member having, a stem portion, adapted for insertion into the intramedullary canal, and a body portion proximal to the stem portion, forming lateral, posterior, and anterior outer side surfaces of the prothesis and configured and dimensioned to accurately fit in the intramedullary canal, said body portion further having a medial side; and a plurality of second members, each said second member connected to the first member, the second member forming anterior, posterior, and medial outer side surfaces of the prothesis and configured and dimensioned for an accurate fit into a differently shaped and sized intramedullary canal, said second members further having a lateral side being substantially the same for each;

wherein the first member together with each said second member defines means for connecting the lateral side of a second member to the medial side of the body portion of the first member such that the combination of the body portion of the first member with the second member forms the anterior and posterior outer side surfaces of the body of the prothesis, the combination configured and dimensioned to accurately fit the intramedullary canal.

12. A kit for the assembly of a hip prosthesis as in claim 11, wherein:

the medial side of the body portion defines a recess configured and dimensioned to receive the lateral sides of the second members, said lateral sides having a shape complimentary therewith; and said connection means includes an element extending from one said member and received in a complimentarily shaped void defined by the other said member.

13. A kit for the assembly of a hip prosthesis as in claim 12, wherein at least one said element comprises a member sized for an interference fit in said void.

14. A kit for the assembly of a hip prosthesis as in claim 15, wherein at least one said member comprises a dovetail.

15. A kit for the assembly of a hip prosthesis as in claim 12, wherein at least one said element comprises a threaded fastener passing through one said member and said void comprises a threaded hole.

16. A kit for the assembly of a hip prosthesis as in claim 12, wherein at least one said recess is defined by a first substantially planar surface on the medial face and a second substantially planar surface disposed at an angle thereto and approximately perpendicular to the anterior and posterior sides.

17. The kit for the assembly of a hip prosthesis as in claim 11, wherein said stem portions are configured and dimensioned to accurately fit into differently shaped and sized intramedullary canals.

18. A kit for the assembly of a hip prosthesis as in claim 11, wherein the lateral, posterior, and anterior surface of at least one body portion includes a porous coating.

19. A modular femoral hip prothesis having distal stem and proximal body sections for implantation into a prepared intramedullary canal comprising:

a first member having, a stem portion forming the stem section of the prothesis and adapted for insertion and an accurate fit within the intramedullary canal;

a body portion proximal to the stem portion and adapted for insertion into the intramedullary canal, the body portion forming the lateral outer side surface and a portion of the anterior and posterior outer side surfaces of the body section of the modular prothesis, said body portion further having a medial side;

a second member connectable with the first member and forming the medial portion of the body section of the modular prothesis, the second member forming the medial outer side surface and a portion of the anterior and posterior outer side surfaces of the body section of the modular prothesis, said second member having a lateral side surface; and means for connecting the lateral side of the second member with the medial side of the first member wherein the body portion of the first member together in combination with the second member forms the outer anterior and posterior surfaces of the body section of the modular prothesis, the combination configured and dimensioned to accurately fit the intramedullary canal.

20. The prosthesis as in claim 19, wherein the first member includes:

a proximally extending neck portion; and a capitulum adapted to replace the head of the femur, the capitulum integrally formed with the neck portion.

* * * * *

UNITED STATES PATENT AND TRADEMARK OFFICE
CERTIFICATE OF CORRECTION

PATENT NO. : 5,549,706

DATED : August 27, 1996

INVENTOR(S) : Thomas F. McCarthy

It is certified that error appears in the above-identified patent and that said Letters Patent is hereby corrected as shown below:

In Claim 14, Column 6, line 12, change "15" to --12--.

Signed and Sealed this

Third Day of December, 1996

Attest:

BRUCE LEHMAN

*Attesting Officer*          *Commissioner of Patents and Trademarks*